(12) United States Patent
Weidmann

(10) Patent No.: US 7,427,760 B2
(45) Date of Patent: Sep. 23, 2008

(54) INFRARED SPECTROMETER

(75) Inventor: Damien Weidmann, Oxfordshire (GB)

(73) Assignee: The Science and Technology Facilities Council, Oxfordshire (GB)

( * ) Notice: Subject to any disclaimer, the term of this patent is extended or adjusted under 35 U.S.C. 154(b) by 0 days.

(21) Appl. No.: 11/606,084

(22) Filed: Nov. 30, 2006

(65) Prior Publication Data

US 2008/0128622 A1    Jun. 5, 2008

(51) Int. Cl.
*G01J 5/62* (2006.01)

(52) U.S. Cl. ..................................... 250/343

(58) Field of Classification Search ............... 250/343, 250/338.1
See application file for complete search history.

(56) References Cited

U.S. PATENT DOCUMENTS

| | | | | |
|---|---|---|---|---|
| 5,317,156 A | * | 5/1994 | Cooper et al. | 250/345 |
| 5,747,809 A | * | 5/1998 | Eckstrom | 250/345 |
| 6,486,474 B1 | * | 11/2002 | Owen et al. | 250/339.02 |

OTHER PUBLICATIONS

High-precision direct measurements of $^{13}CH_4/^{12}CH_4$ and $^{12}CH_3D/^{12}CH_4$ ratios in atmospheric methane sources by means of a long-path tunable diode laser absorption spectrometer; Peter Bergamaschi et al.; Applied Optics; vol. 33, No. 33; Nov. 20, 1994; pp. 7704-7716.
Fast gas spectroscopy using pulsed quantum cascade lasers; T. Beyer, M. Braun and A. Lambrecht; Journal of Applied Physics; vol. 93, No. 6; Mar. 15, 2003; pp. 3158-3160.
First field determination of the $^{13}C/^{12}C$ isotope ratio in volcanic $CO_2$ by diode-laser spectrometry; A. Castrillo, G. Casa, M. van Burgel, D. Tedesco and L. Gianfrani; Optics Express; vol. 12, No. 26; Dec. 27, 2004; pp. 6515-6523.
High-precision determination of the $^{13}CO_2/^{12}CO_2$ isotope ratio using a portable 2.008-µm diode-laser spectrometer; G. Gagliardi, A. Castrillo, R.Q. Iannone, E.R.T. Kerstel, L. Gianfrani; Applied Physics; B 77; Aug. 12, 2003; pp. 119-124.

(Continued)

*Primary Examiner*—David P. Porta
*Assistant Examiner*—Marcus H Taningco
(74) *Attorney, Agent, or Firm*—Birch, Stewart, Kolasch & Birch, LLP

(57) ABSTRACT

Method and apparatus for detecting, by absorption spectroscopy, an isotopic ratio of a sample, by passing first and second laser beams of different frequencies through the sample. Two IR absorption cells are used, a first containing a reference gas of known isotopic ratio and the second containing a sample of unknown isotopic ratio. An interlacer or reflective chopper may be used so that as the laser frequencies are scanned the absorption of the sample cell and the reference cell are detected alternately. This ensures that the apparatus is continuously calibrated and rejects the baseline noise when phase sensitive detection is used.

32 Claims, 6 Drawing Sheets

OTHER PUBLICATIONS

Development of a compact quantum cascade laser spectrometer for field measurements of $CO_2$ isotopes; D. Weidmann, G. Wysocki, C. Oppenheimer, F.K. Tittel; Applied Physics; B 80; 2005; pp. 255-260.

$^{13}CO_2/^{12}CO_2$ isotopic ratio measurments using a difference frequency-based sensor operating at 4.35 μm; M. Erdelyi, D. Richter, F.K. Tittel; Applied Physics; B 75; 2002; pp. 289-295.

Fast, real-time spectrometer based on a pulsed quantum-cascade laser; E. Normand, M. McCulloch, G. Duxbury and N. Langford; Optics Letters; vol. 28, No. 1; Jan. 1, 2003; pp. 16-18.

Mid-infrared trace-gas sensing with a quasicontinuous-wave Peltier-cooled distributed feedback quantum cascade laser; E. Weidmann, F.K. Tittel, T. Aellen, M. Beck, D. Hofstetter, J. Faist, S. Blaser; Applied Physics; B79; Sep. 29, 2004; pp. 907-913.

Low-threshold continous-wave operation of quantum-cascade lasers grown by metalorganic vapor phase epitaxy; Mariano Troccoli, David Bour, Scott Corzine, Gloria Hofler, Ashish Tandon and Dan Mars, David J. Smith, Laurent Diehl and Federico Capasso; Applied Physics Letters; vol. 85, No. 24; Dec. 13, 2004; pp. 5842-5844.

Development of a tunable mid-IR difference frequency laser source for highly sensitive airborne trace gas detection; D. Richter, A. Fried, B.P. Wert, J.G. Walega, F.K. Tittel; Applied Physics; B75; Apr. 29, 2002; pp. 281-288.

Spectroscopic performance evaluation of optical fiber amplified coherent diode and fiber laser sources for difference frequency generation; Dirk Richter, Alan Fried, Christoph Dyroff and James G. Walega; Optical Society of America; 2004; LACEA Conference, MD, Feb. 11, 2004.

* cited by examiner

INFRARED SPECTROMETER

FIELD OF THE INVENTION

The present invention relates to a infrared, IR, spectrometer and in particular to a tunable IR laser spectrometer.

The present invention also relates to a method of isotopic ratio determination and a method of selecting a pair of isotopic spectroscopic lines for a sample suitable for use in isotopic ratio determination.

BACKGROUND OF THE INVENTION

Stable isotopomer concentration and flux measurements have become a vital underpinning technique in many areas of science. To date, mass spectrometry (MS) has been the preferred technique to perform isotope analysis. For any application requiring real time, high frequency data, and/or field measurements, MS suffers from drawbacks: tedious sample taking and preparation, difficulty of real time analysis. Furthermore, MS' does not resolve small mass differences particularly well. The use of MS is confined to a dedicated laboratory and field applications are therefore difficult. There is a growing need to overcome these drawbacks and to seek alternative instrumentation for high precision (~0.1‰) isotopic ratio determination both in the academic and industrial sectors. Applications encompass atmospheric studies, geology, ecology, medical research, planetary exploration, combustion science, fundamental analytical chemistry, and food industry quality check.

Therefore, there is requirement for a method and apparatus for providing high precision isotopomer concentration and ratio measurements without the above drawbacks.

SUMMARY OF THE INVENTION

Generally, the present invention provides a method and apparatus for detecting, by absorption spectroscopy, an isotopic ratio of a sample, by passing first and second laser beams of different frequencies through the sample. In a particular example, this may be applied to the determination of $^{12}CO_2$:$^{13}CO_2$ or similar.

Typically, two IR absorption cells are used, a first containing a reference gas of known isotopic ratio and the second containing a sample of unknown isotopic ratio. Advantageously, an interlacer, switcher or reflective chopper may be used so that as the laser frequencies are scanned the absorption of the sample cell and the reference cell are detected alternately. This ensures that the apparatus is continuously calibrated and rejects the baseline noise when phase sensitive detection is used.

Further details of the present invention are described in the accompanying claims.

BRIEF DESCRIPTION OF THE FIGURES

The present invention may be put into practice in a number of ways and an embodiment will now be described by way of example only and with reference to the accompanying drawings, in which.

DETAILED DESCRIPTION OF AN EMBODIMENT

The inventor of the present invention has described carbon isotopomer ratio measurements in "Carbon isotopomers measurement using mid-IR tunable laser sources" Damien Weidmann, et al, Isotopes in Environmental and Health Studies, Vol. 41, No. 4, December 2005, pp 293-302 (DOI: 10.1080/10256010500384325), which is incorporated by reference in its entirety herein.

Absorption spectroscopy techniques, using infrared laser sources, offer an improvement over MS. A useful spectral region for absorption spectroscopy is known as the "fingerprint" region lying in the mid infrared range (2-25 µm), where most molecules exhibit intense vibrational transitions.

As an example, identification and measurement of gases released by volcanoes provide information on magmatic sources and so aid interpretation of volcanic behaviour and eruption forecasting. As well as information on real-time trace gas concentrations in volcanic emissions, isotopic ratio measurements of species including carbon, hydrogen, nitrogen, oxygen and sulphur provide additional information concerning the gas sources and their geochemical history. Stable carbon isotopomers, especially $^{12}CO_2$ and $^{13}CO_2$, are of particular interest. Carbon dioxide is typically the most abundant gas released by volcanoes after $H_2O$. $^{13/12}CO_2$ monitoring can be used as a tracer to discriminate the sources contributing to observed $CO_2$ emissions.

Figure 1:
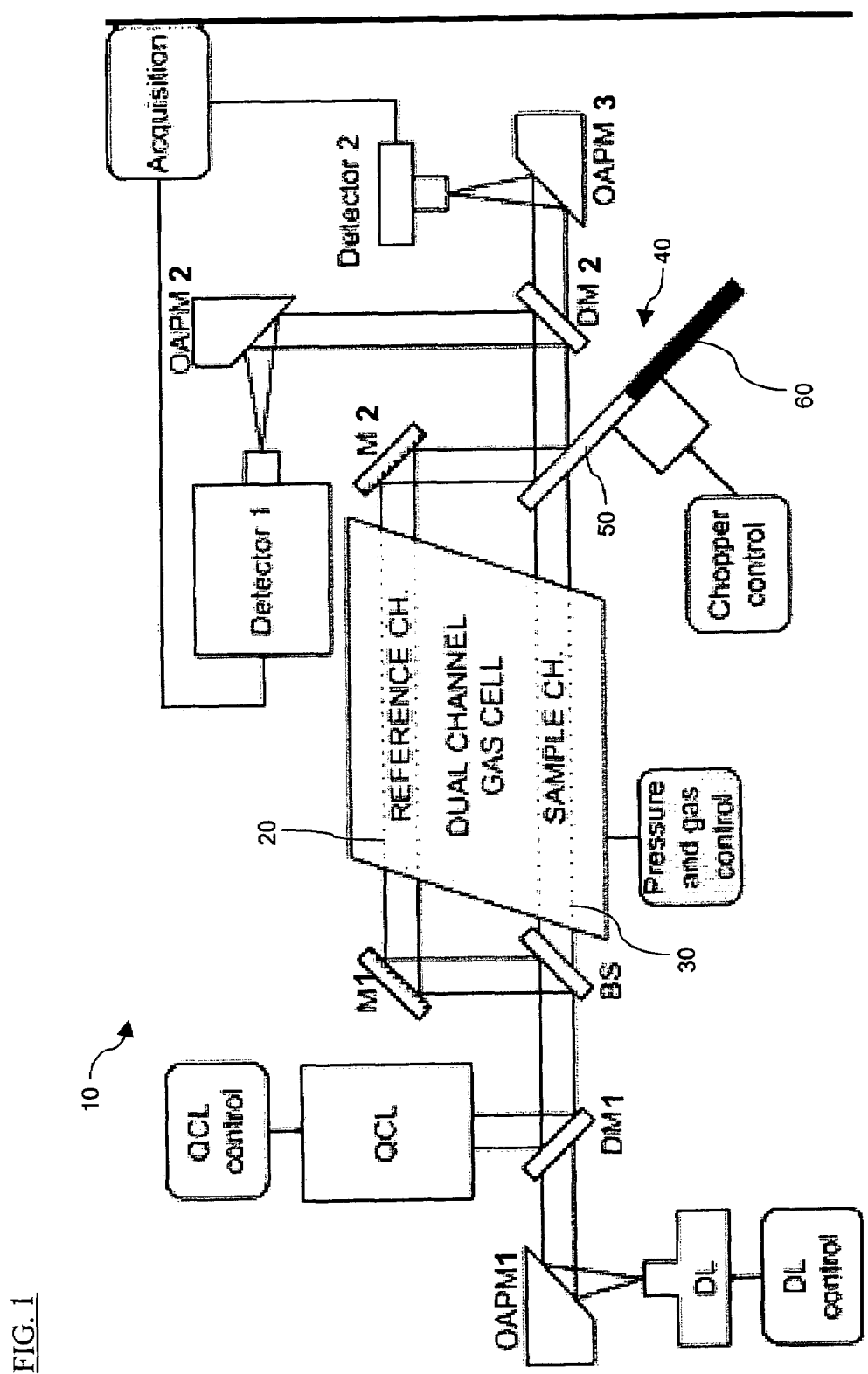
FIG. 1 shows a schematic diagram of an IR laser spectrometer according to a first embodiment of the present invention, given by way of example only.

FIG. 1 shows a schematic diagram of an IR spectrometer 10 according to a first embodiment of the present invention.

Diode laser DL is a room temperature tunable antimonide laser operating around 3601 cm$^{-1}$. Quantum cascade laser QCL is a room temperature tunable laser operating around 2294 cm$^{-1}$. Off-axis parabolic mirror OAPM1 collimates the beam from the QCL and this collimated beam is combined with the beam from DL using a dichroic mirror DM1.

The combined beam is then split into two paths by a beam splitter BS before each portion of the beam enters a dual channel absorption cell providing the sample-laser interaction volume. Mirror M1 directs one of the split beams into channel 20, whilst the portion passing through the beam splitter enters channel 30 directly. The beams may be split 50:50 or by any other ratio. Channel 20 contains a reference sample of known composition and channel 30 contains a sample under investigation. For instance channel 20 may contain a mixture of $^{12}CO_2/^{13}CO_2$ of known proportion and channel 30 may contain a mixture of $^{12}CO_2/^{13}CO_2$ of unknown proportion. The pressure, flow rate and temperature of the sample and reference may be controlled and monitored during absorption measurements.

As two wavelengths probe each cell channel, the system performs measurements over four spectroscopic channels.

Detector 1 and detector 2 detect transmitted laser light originating from the DL and QCL respectively. Detector 1 and detector 2 are each respectively sensitive to the wavelengths provided by the DL and QCL lasers. Dichroic mirror DM2 separates the combined beam ensuring that detector 1 receives light originating from the DL and detector 2 receives light originating from the QCL. Off-axis parabolic mirrors QAPM1 and QAPM2 focus the collimated beams onto detectors 1 and 2 respectively.

At the output of the dual channel absorption cell a 10 KHz chopper 40 with reflective blades plays the role of an interlacer. Mirror M2 directs the output of channel 20 onto the chopper blades. With the chopper 40 presenting an opening 50 towards the output of the dual absorption cell the output of channel 20 (reference) passes straight through and is not directed towards the two detectors. However, the output from channel 30 (sample) also passes straight through the chopper and is directed onto the two detectors.

With the chopper 40 presenting a reflective blade towards the output of the dual absorption cell the output of channel 30 is blocked by the back of the mirror and the output from channel 20 (reference) is directed onto the two detectors. In this way detectors 1 and 2 sequentially receive IR radiation transmitted through each channel 20, 30 in turn. An acquisition unit collects and stores data from each of the two detectors. The acquisition unit may be in turn connected to a computer system for data manipulation and storage. Alternately, the computer system itself may act as the acquisition unit.

The DL and QCL lasers are each tunable across a range of wavelengths. DL control controls the output wavelength of diode laser DL. QCL control controls the output wavelength of the QCL laser. The wavelengths of each laser are scanned across a particular range in order to obtain an absorption spectrum from the reference and sample with intensity being measured by the two detectors. The tuning of each laser is synchronised such that a step change intensity occurs after each cycle (open, reflective blade) of the chopper. Alternatively, instead of a step change, a smooth continuous wavelength change may be made.

The alternate sampling of the reference cell 20 and sample cell 30 provides an effective onboard calibration.

Figure 6A:
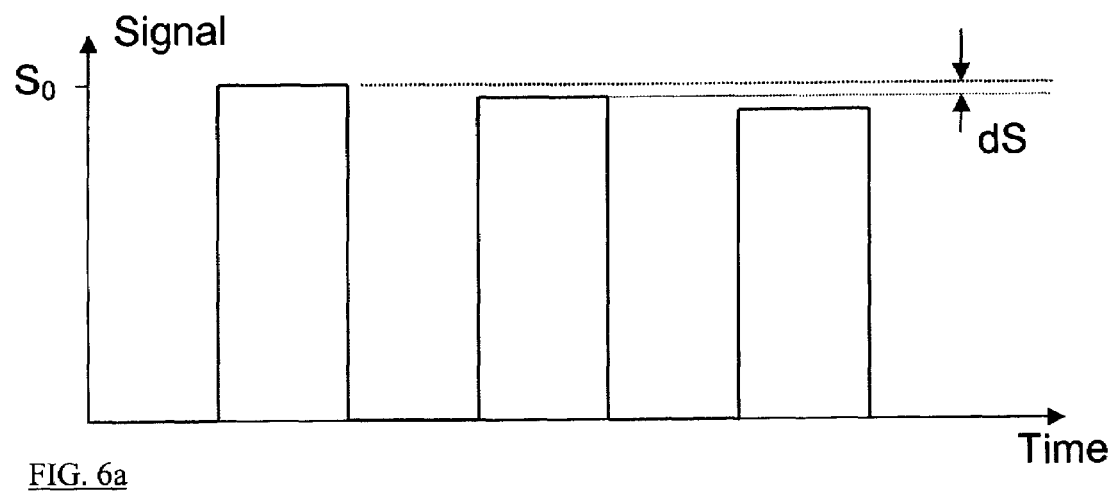
FIG. 6a shows a graph illustrating conventional phase sensitive detection in tunable spectroscopy using a chopper.

FIG. 6a shows a schematic illustration of conventional phase sensitive detection in tunable spectroscopy using a chopper. The signal peak to peak amplitude is $S_0$ and only a small variation dS of this amplitude contains useful information.

Figure 6B:
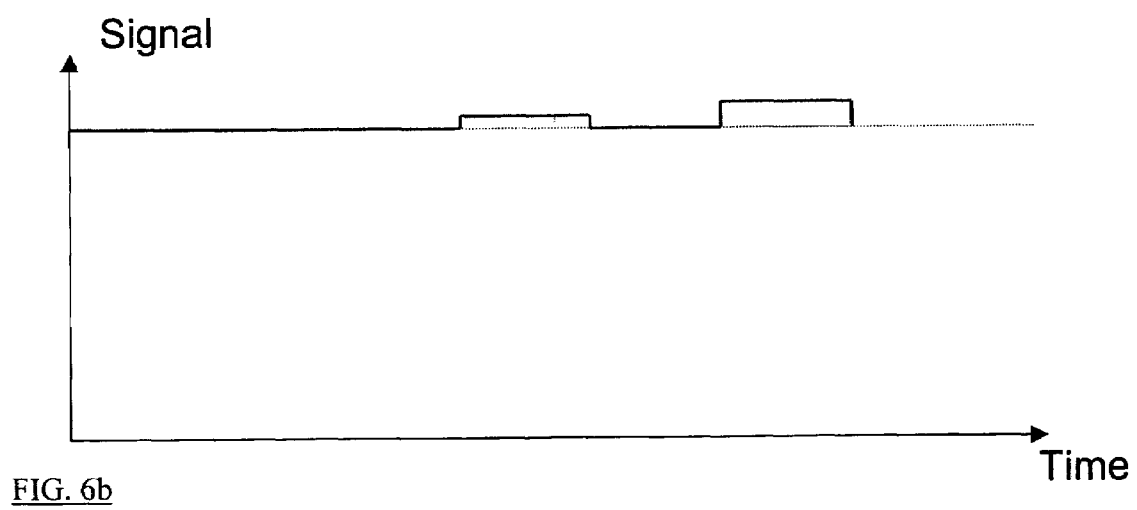
FIG. 6b shows a graph illustrating the signal obtained using the IR laser spectrometer of FIG. 1.

FIG. 6b shows a schematic illustration of the signal obtained from the present invention using a reflective chopper. The signal peak to peak amplitude is dS. AC levels of amplification can be much higher as only the change is monitored. Other drifting parameters cancel out using such a technique with phase sensitive detection.

Figure 2:
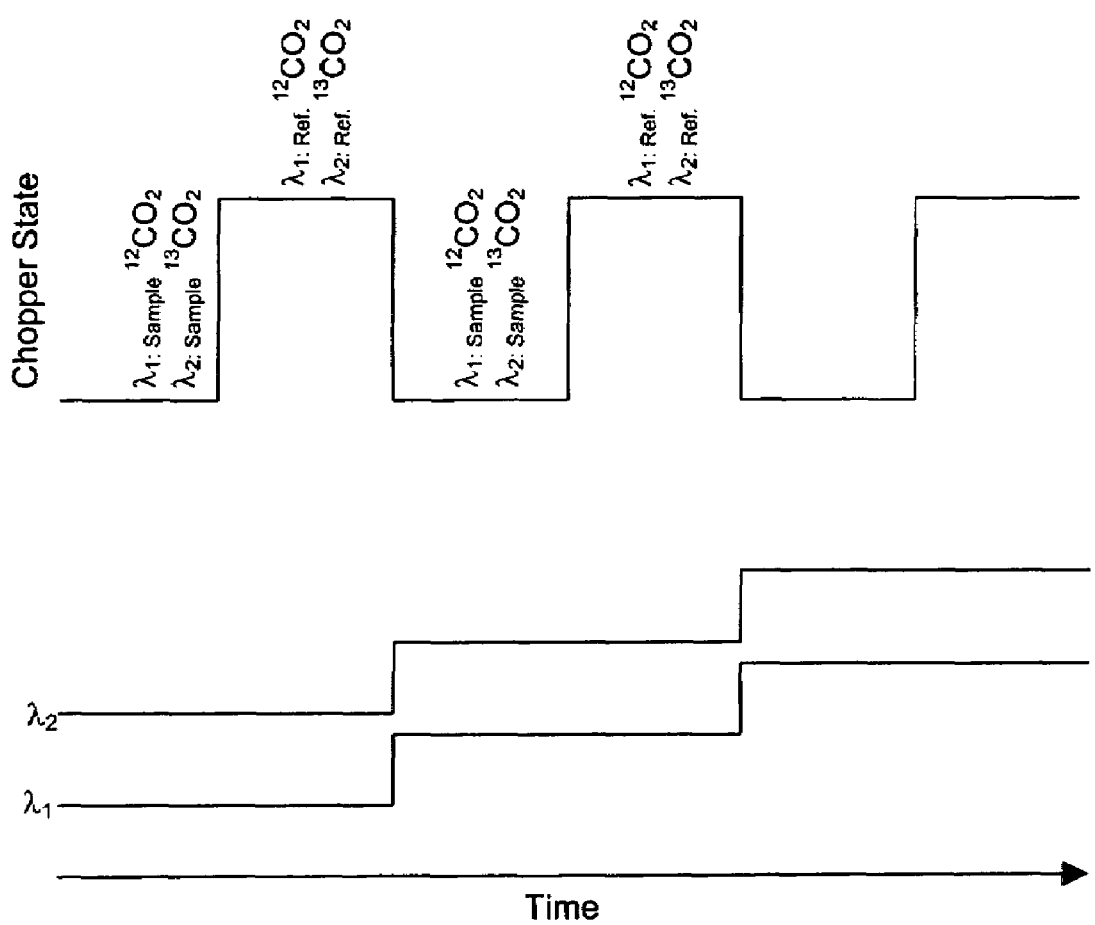
FIG. 2 shows a timeline of the data acquired from the IR laser spectrometer of FIG. 1.

FIG. 2 shows the timeline showing the synchronisation between the laser tuning for each laser (having wavelength $\lambda_1$ and $\lambda_2$, respectively) and the chopper state, i.e. which of cell 20 (reference) or 30 (sample) is being measured by detectors 1 and 2. Note that each laser wavelength changes at the same time once a reference/sample cycle has been completed. It is not necessary that the wavelength of each laser changes at the same rate. Alternatively, a smooth variation of wavelength may occur throughout the cycle.

Isotopic ratio is usually expressed in terms of delta value defined by equation 1:

$$\delta = \left(\frac{R_X}{R_S} - 1\right) \times 1000 \qquad \text{Equation 1}$$

where $R_X$ denotes the ratio of the heavier isotope to the lighter one in the sample to be measured, and $R_S$ refers to the ratio of a calibrated reference sample. Units are "per mil" or ‰.

Figure 3:
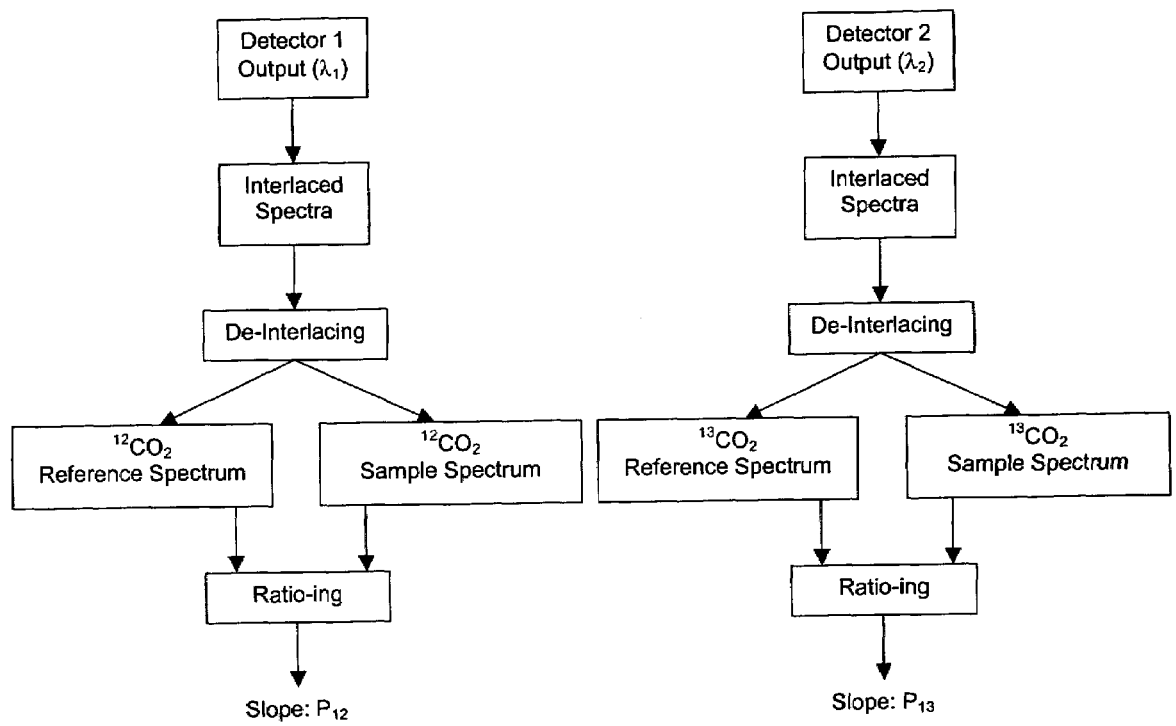
FIG. 3 shows a flow-chart of a method of collecting data from the IR laser spectrometer of FIG. 1.

FIG. 3 shows a flow diagram of a method of obtaining a relative delta value, $\delta_{rel}$ of a $CO_2$ sample. In this case:

$$\delta_{rel} = \frac{P_{13}}{P_{S12}} - 1 \qquad \text{Equation 2}$$

Figure 4:
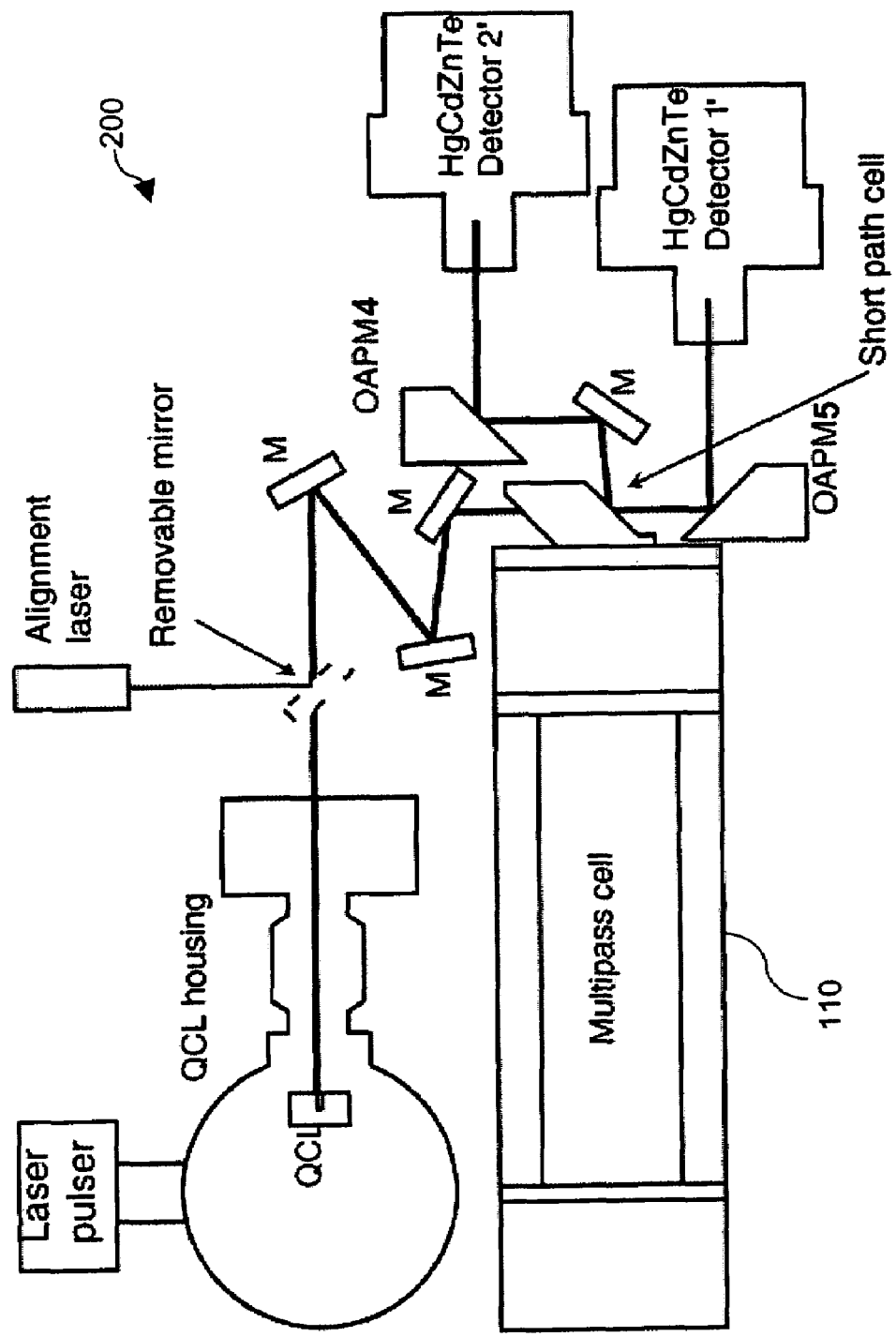
FIG. 4 shows an IR laser spectrometer according to a second embodiment of the present invention, given by way of example only.

FIG. 4 shows a QCL-based two channel spectrometer 200. This two channel spectrometer allows isotopomer measures to be made for certain pairs of spectroscopic lines but has limited functionality when compared with spectrometer 10 of FIG. 1. The identified target lines for this sensor may be located at 2311.105566 cm$^{-1}$ ($^{12}CO_2$, v3) and 2311.398738 cm$^{-1}$ ($^{13}CO_2$, v3), respectively. With this selection, the $\delta^{13}C$ measurements are insensitive to gas temperature variations. However, the line intensities differ by a factor of about 100, and therefore a dual path length absorption cell is required. The sensor has already been described in "Development of a compact quantum cascade laser spectrometer for field measurements of $CO_2$ isotopes", Appl. Phys. B, 80, pp 255-260 (2005), incorporated by reference herein. The spectroscopic source is a pulsed, thermoelectrically cooled, DFB QC laser excited by 25 ns current pulses. A dual path length absorption cell 110 is an astigmatic Herriott cell modified to incorporate an additional short path. After exiting the cells, the two beams are directed to two thermoelectrically cooled HgCdZnTe detectors. The complete optical subsystem is housed inside a sealed Delrin case and purged with dry nitrogen to avoid contamination from atmospheric $CO_2$ or corrosive gases. The associated sensor electronics are located below the optical platform. A gas control subsystem alternating the flow of sample and calibration gases into the absorption cell is connected to the instrument. The operating wavelength of the QCL obtained for this system was found to be 0.8 cm$^{-1}$ distant from the selected frequencies. Also, an unusually large threshold current (9 A) prevented the use of a fast (0.400 Hz) subthreshold current ramp to rapidly tune the laser wavelength. A $^{12}CO_2$ line at 2320.7501 cm$^{-1}$ and a $^{16}O^{12}C^{18}O$ line at 2320.4599 cm$^{-1}$ may be targeted with this device. The intensity ratio of these lines is 0.20 The extrapolated precision of $\delta^{13}C$ is 0.1‰. Because a single laser source is used in spectrometer 200 only close absorption lines may be investigated. Furthermore, the use of a single cell requires separate reference calibration once a sample has been purged.

Before spectroscopic measurements may be taken a suitable pair of spectroscopic absorption lines must be identified. In order to avoid the need for different path lengths within the absorption cells (such as used in spectrometer 200) lines of similar intensity may be chosen. As this technique relies on measuring absolute absorption line intensities the overriding requirement is to avoid lines which behave differently to temperature changes. Ideally, the relative change in intensity for each line in a pair when the temperature varies will be the same. With single laser spectrometers the choice of lines is limited to lines very close together. This leads to difficulty in resolving the lines and usually results in large differences in absolute line intensities. However, with the availability of the dual lasers system of the present invention lines very far apart in wavelength terms may be used as a pair.

In a further aspect of the present invention there is provided a method of choosing isotopic spectroscopic lines. This line selection method, which consists of choosing optimum absorption lines for the two isotopomers under study, involves the consideration of several issues.

The line intensities have to be considered. Ideally, similar intensities would be sought so that the same cell can be used (i.e. same path length), and to limit potential non-linearities in the detection system. The line intensities should also be high enough to ensure the best sensor sensitivity and to allow the use of a compact absorption cell. The temperature stability requirement depends on the Boltzmann distribution of the two respective isotopic transitions. A similar evolution of the two line intensities with temperature is important to limit sensitivity to temperature fluctuations. This condition is expressed equation3:

$$\Delta T \cdot \Delta E = \Delta \delta \cdot k \cdot T^2 \qquad \text{Equation 3}$$

where $\Delta\delta$ is the target accuracy on $\delta$, k the Boltzmann constant, T the temperature, $\Delta E$ the energy difference between the lower levels of the two transitions and $\Delta T$ the temperature variation. Hence, in terms of spectroscopic parameters to obtain temperature insensitivity, the lower energy levels must be identical.

The potential spectral and collisional interferences by other species have to be considered. In particular, it is important to avoid interference due to water vapour. Well isolated lines are preferred, making concentration retrievals easier. Other parameters may be dictated by the spectroscopic source to be used. For example, ensuring that the two lines are within the available tuning range and that the source linewidth matches the absorption widths of the selected isotopic line pair.

To implement line selection for any pair of isotopomers of any molecule, an algorithm based on the aforementioned method may be used. First, depending on the experimental conditions, the minimum line intensities to be considered may be defined (cutoff intensity, $S_{min}$). Then, precision parameters may be entered into the algorithm: the minimum acceptable temperature stability $\Delta T$, the relative difference allowed between the two line intensities $\Delta S$ and the minimum frequency separation required between the two lines $\Delta v$. All the possible line pairs of the two selected isotopomers within the available database are then processed. The identified line pairs then have to be critically examined, taking into account the other aforementioned selection criteria.

The algorithm may be applied to potential $^{12}CO_2$, $^{13}CO_2$ line pairs or any other suitable molecule. The minimum intensity may be set to 10-21 $cm^{-1}/molec\ cm^{-2}$. This intensity criterion is low for atmospheric studies, but sufficient for volcanic environments where $CO^2$ concentrations can exceed several percent.

The parameters may be chosen as follows: a target delta value accuracy of 0.1‰, a temperature stability of better than 0.5 K, a relative difference in intensities of <10% and line separation of at least 0.05 $cm^{-1}$. A stringent condition on line intensities is required to achieve the expected accuracy on the delta value.

Figure 5:
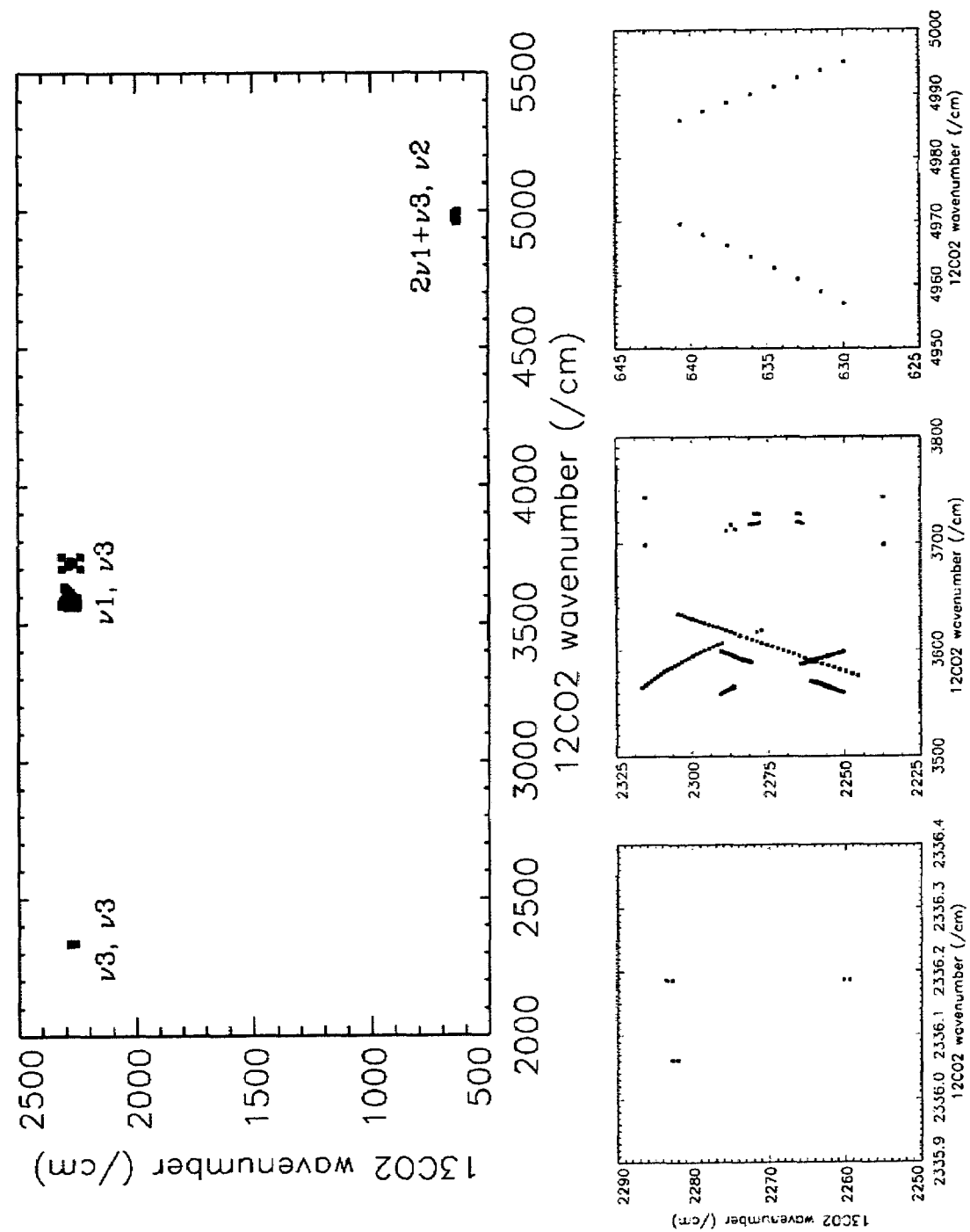
FIG. 5 shows a set of graphs depicting pairs of suitable spectral lines to be investigated by the IR laser spectrometer of FIG. 1 or FIG. 4.

FIG. 5 shows the results of applying the above algorithm to the spectroscopic lines of $^{12}CO_2$ and $^{13}CO_2$. The lower graph provides details of the three ro-vibrational band intersections appearing in the main graph: (v3, v3), (v1, v3), (2v1+v3, v2), from left to right. One hundred and eighty-eight pairs of transitions satisfy these criteria. The points are located in three regions, detailed in the lower part of FIG. 5, corresponding to the intersection of the $^{12}CO_2$ and $^{13}CO_2$ bands indicated on the upper graph.

FIG. 5 indicates that the optimum selection involves two lines from two different bands, thus requiring the two laser sources of the present invention. With the parameters used to establish this selection, only two pairs belong to the same band (v3) and the smallest frequency separation is found to be 0.25 $cm^{-1}$ for 2336.5590 $cm^{-1}$ ($^{13}CO_2$) and 2311.3990 $cm^{-1}$ ($^{12}CO_2$). Such a tuning range is not accessible from a single semiconductor mid-IR sources.

By choosing more stringent parameters such as $S_{min}$=10-20 $cm^{-1}/molec\ cm^{-2}$, $\Delta T$=10K, $\Delta S$=1%, only three line pairs are found. They are listed in table 1.

TABLE 1

Optimum line selection for $^{13/12}CO_2$ ratio measurements.

| $^{12}CO_2$ | | | $^{13}CO_2$ | | |
|---|---|---|---|---|---|
| Frequency ($cm^{-1}$) | Strength ($cm^{-1}/molec\ cm^{-2}$) | Band | Frequency ($cm^{-1}$) | Strength ($cm^{-2}/molec\ cm^{-2}$) | Band |
| 3601.4210 | 3.513e−020 | v1 + v3 | 2294.4811 | 3.547e−020 | v3 |
| 3599.7027 | 3.573e−020 | v1 + v3 | 2295.8456 | 3.574e−020 | v3 |
| 3597.9626 | 3.525e−020 | v1 + v3 | 2297.1862 | 3.499e−020 | v3 |

These three line pairs offer the best strategy to achieve a high accuracy for $\delta^{13}C$ measurements.

The line pair selection may be made so that both the two intensities and the two absorption frequencies are close. Inherently, the lower state energies of the selected line pair are different, $\Delta E$ 1160 $cm^{-1}$. The expected required temperature stability, calculated with equation 3, is 6 mK. As a consequence, pressure change has a strong effect on the peak amplitude and overlapping wing contributions from one line to the other.

The present invention may be used in:

Geophysical studies: Real time continuous monitoring of isotopomers released by volcanic fumes. The knowledge of isotope concentrations allows the deduction of information about the different sources feeding a volcanic system. The present invention strengthens the reliability of volcanic eruption forecasting. Also oil prospecting can be facilitated by identifying carbon sources using this method.

Atmospheric & environmental sensing: The present invention allows the provision of high temporal and high spatial resolution $^{13}C/^{12}C$ data, thus providing further constraint to carbon budget models. This allows a fuller understanding and account for carbon sources and sinks.

Planetary exploration: The present invention may be used in planetary exploration, especially Mars exploration.

Medical diagnostics: Real time, continuous monitoring of trace molecule enables non-invasive breath diagnostics. For instance, the activity of Pylobacter Pylori (bacteria responsible of stomach ulcer) may be identified by the measurement of $^{12}CO_2/^{13}CO_2$ ratio in breath. $^{12}C/^{13}C$ ratio may also discriminate between a catabolic and anabolic state of living cells.

Agronomy and food industry: Isotopomers concentration contained in a given product may indicate the product origin. Real time, continuous monitoring of isotopic ratio by the present invention may provide on-line implementation, and detection of artificial substitutes.

As will be appreciated by the skilled person, details of the above embodiments may be varied without departing from the scope of the present invention.

For example, the chopper may be placed before the absorption cells 20, 30 to alternately block or switch the incident IR beams rather than blocking the transmitted beams. In this alternative embodiment the beam splitter may not be required resulting in all of the available laser intensity being incident on one cell at a time. Obviously, the detector arrangement will require adjustment accordingly.

A single detector may be used provided that it can detect both wavelengths.

Although a 10 kHz chopper frequency has been described, any suitable frequency may be used.

Preferred embodiments and methods of the present invention discussed in the foregoing are to be understood as descriptions for illustrative purposes only, and it will be appreciated that numerous changes, substitutions, omissions, and updates thereof are possible without departing from the spirit and scope of the claims.

The invention claimed is:

1. An infrared, IR spectrometer comprising:
    a first tunable IR laser for providing a first beam at a first wavelength;
    a second tunable IR laser for providing a second beam at a second wavelength;
    a first absorption cell arranged to receive both first and second beams;
    a second absorption cell arranged to receive both first and second beams;
    a first optical absorption detector arranged to detect said first wavelength;
    a second optical absorption detector arranged to detect said second wavelength; and
    an interlacer arranged to alternately block said first and said second absorption cells,
    wherein said interlacer is an optical chopper comprising at least one reflective blade angled to direct transmitted IR radiation from one of said optical absorption cells on to both of said optical absorption detectors.

2. The IR spectrometer of claim 1 further comprising a beam combiner arranged to combine said first beam with said second beam to form a combined beam such that said first absorption cell and said second absorption cell each receive a portion of said combined beam.

3. The IR spectrometer of claim 1, wherein said beam combiner comprises a dichroic mirror.

4. The IR spectrometer of claim 1, further comprising a beam splitter arranged to direct a portion of the combined beam into each of said first and second absorption cells.

5. The IR spectrometer of claim 1 further comprising a beam separator arranged to separate said first wavelength from said second wavelength such that said first wavelength is detected by said first detector and said second wavelength is detected by said second detector.

6. The IR spectrometer of claim 1, wherein said first tunable IR laser is a diode laser.

7. The IR spectrometer of claim 6, wherein said diode laser is tunable between about 2 μm and about 12 μm.

8. The IR spectrometer of claim 1, wherein said second tunable IR laser is a quantum cascade laser.

9. The IR spectrometer of claim 8, wherein said quantum cascade laser is tunable between about 4 μm and about 24 μm.

10. The IR spectrometer of claim 1 further comprising a data logger for recording data generated by said first and second optical absorption detectors.

11. The IR spectrometer of claim 1, wherein said first absorption cell contains a reference sample and said second absorption cell contains a sample.

12. The IR spectrometer of claim 1, wherein the wavelengths of said first and second tunable IR lasers are changeable after said first and said second optical absorption detectors have been blocked.

13. The IR spectrometer of claim 1, wherein the first wavelength is different to the second wavelength.

14. The IR spectrometer of claim 1, wherein said first and second absorption cells contain a sample consisting of one of $^{12}CO_2/^{13}CO_2$, $C^{16}O_2/^{16}OC^{18}O$, $H_2^{16}O/H_2^{18}O$, $^{12}CH_4/^{13}CH_4$, $^{12}CH_4/^{12}CDH_3$, $^{14}N_2O/^{14}N^{15}NO$ and $H_2O/HDO$.

15. The IR spectrometer of claim 1, wherein the first and second IR tunable lasers are arranged to vary the first and second wavelengths in synchronisation with the optical chopper.

16. The IR spectrometer of claim 15, wherein the first and second wavelengths are arranged to vary stepwise.

17. The IR spectrometer of claim 15, wherein the first and second wavelengths are arranged to vary smoothly.

18. The IR spectrometer of claim 15, wherein the first and second wavelengths are arranged to be varied across a selection of absorption lines of a sample being measured.

19. The IR spectrometer of claim 15, wherein the optical chopper is arranged to direct transmitted IR radiation from one of said optical absorption cells on to both of said optical absorption detectors at a frequency.

20. The IR spectrometer of claim 19, wherein the first and second optical absorption detectors are arranged to detect at the frequency.

21. The IR Spectrometer of claim 20, wherein the detection is maintained at the frequency by phase detection of the chopper frequency.

22. The IR Spectrometer claim 1, wherein the interlacer alternatively blocks said first and said second absorption cells at or above 1 KHz.

23. An infrared, IR, spectrometer comprising:
    a first tunable IR laser for providing a first beam at a first wavelength;
    a second tunable IR laser for providing second beam at a second wavelength;
    a first absorption cell arranged to receive both first and second beams;
    a second absorption cell arranged to receive both first and second beams;
    a first optical absorption detector arranged to detect said first wavelength;
    a second optical absorption detector arranged to detect said second wavelength; and
    an interlacer arranged such that said first and said second absorption cells are alternately switched from receiving said first and said second beams.

24. A method of isotopic ratio determination comprising the steps of:
    (a) passing a first tunable IR laser beam through a first absorption cell;
    (b) passing a second tunable IR laser beam through a second absorption cell;
    (c) detecting the absorption due to a first sample contained within said first cell; and
    (d) detecting the absorption due to a second sample contained within said second cell such that the isotopic ratio of said second sample is determined; and
    (e) alternately switching said first and second IR laser beams such that the detecting steps (c) and (d) occur in turn.

25. The method of claim 24 further comprising the step of:

(i) combining said first tunable IR laser beam with said second tunable IR laser beam before passing both laser beams through both cells.

26. The method of claim 24 further comprising the step of varying the wavelength of each tunable IR laser beam following each sequence of step (c) and (d).

27. The method of claim 26, wherein the wavelength of each tunable IR laser is varied stepwise.

28. The method of claim 26, wherein the wavelength of each tunable IR laser is varied smoothly.

29. The method of claim 26, wherein the wavelength is varied across a selection of absorption lines of a sample being measured.

30. The method of claim 26, wherein the first and second IR laser beams are alternatively switched at a frequency and detecting the absorption due to the first and second samples occurs at the frequency.

31. The method of claim 30, wherein the detection is maintained at the frequency by phase detection.

32. The method of claim 30, wherein the frequency is at or above 1 KHz.

* * * * *